United States Patent [19]

Takayama et al.

[11] Patent Number: 5,034,327
[45] Date of Patent: Jul. 23, 1991

[54] METHOD FOR PROPAGATION OF POTATOES

[75] Inventors: Shinsaku Takayama; Motomu Akita, both of Ibaraki, Japan

[73] Assignee: Kyowa Hakko Kogyo Co., Ltd., Tokyo, Japan

[21] Appl. No.: 442,431

[22] Filed: Nov. 21, 1989

Related U.S. Application Data

[63] Continuation of Ser. No. 251,225, filed as PCT JP87/00923 on Nov. 27, 1987, published as WO88/04136 on Jun. 16, 1988, abandoned.

[30] Foreign Application Priority Data

Dec. 2, 1986 [JP] Japan .................. 61-287213

[51] Int. Cl.$^5$ .......................... A01C 1/00; C12N 5/04
[52] U.S. Cl. .................... 435/240.4; 47/58; 47/DIG. 3; 435/240.45; 435/240.46; 435/240.51
[58] Field of Search ............... 47/58, DIG. 3; 435/240.4, 240.45, 240.46, 240.51

[56] References Cited

U.S. PATENT DOCUMENTS 4,115,950 9/1978 Lantai .
4,569,914 2/1986 Molnar et al. .

FOREIGN PATENT DOCUMENTS

| 098234 | 1/1984 | European Pat. Off. . |
| 3734257 | 4/1989 | Fed. Rep. of Germany .......... 47/58 |
| 55-118319 | 7/1980 | Japan ................ 47/DIG. 3 |
| 55-43723 | 11/1980 | Japan ................ 47/DIG. 3 |
| 0078381 | 4/1986 | Japan ................ 435/240.45 |

OTHER PUBLICATIONS

Annals of Botany 53, 565-578 (1984), Hussey et al., "Factors Affecting the Formation . . . ".
Potato Physiology 1985, Academic Press, pp. 503-577, "Potato Tissue Culture and its Applications in Agriculture", Wang.
American Potato Journal 60, 27-33 (1983), Wattemina et al.
"Comparative Field Performance of Potatoes from Microculture".
American Potato Journal 59, 33-37 (1982), Want and Hu, "Invitro Mass Tuberization . . . ".
Wang, P. et al., (1982), "*In vitro* Mass Tuberization and Virus-Free Seed-Potato Production in Taiwan", *Am. Potato J.*, vol. 59, pp. 33-37.
Abbott, A. J. et al. (1986), "Potato Tuber Formation in vitro", *Plant Tissue Culture and Its Agricultural Applications* Butterworths Publish., pp. 113-122.
Estrada, R. et al., (1986), "Induction of in vitro Tubers in a Broad Range of Potato Genotypes", *Plant Cell Tissue and Organ Culture*, vol. 7, pp. 3-10.
Ammirato, P. (1984), "Section V Root and Tuber Crops: Chapt. 11, Potato", *Handbook of Plant Cell Culture* Pub. MacMillan Publishing Co., N.Y., New York, pp. 291-295-298, 309-311, 317-321, 322-326.
American Potato Journal 60, 27-33, (1983), "Comparative Field Performance of Potatoes from Microculture".
American Potato Journal, 55, 691-701 (1978), "A Tissue Culture Method for the Rapid Propagation of Potatoes".
Soshiki Baiyo 11(9), 391-395 (1985).
Soshiki Baiyo 11(9), 372-376 (1985).

*Primary Examiner*—James R. Feyrer
*Attorney, Agent, or Firm*—Michael N. Meller

[57] ABSTRACT

The present invention relates to a method of obtaining, on a large scale by tissue culture, tuber of potato, corm of taro, konjak, jack-in-the-culprit, rhizome of Scopolia japonica, tuberous root of Chinese yam, etc. having an enough large size to cultivate seed tubers by one cultivation in the soil. This method comprises culturing the plant itself or its slices in a liquid medium till the plant grows to a size of 15 to 30 cm on the average, sinking 90% or more of the plant in the liquid medium, while further performing cultivation, reducing the amount of the liquid medium with passage of time to such a degree that 50 to 98% of the plant is exposed into the aerial phase to thereby obtain a large amount of tuber, corm, rhizome or tuberous root in a short time.

1 Claim, No Drawings

METHOD FOR PROPAGATION OF POTATOES

This application is a continuation of application Ser. No. 251225, filed as PCT JP87/00923 on Nov. 27, 1987, published as WO88/04136 on Jun. 16, 1988, abandoned.

FIELD OF THE INVENTION

The present invention relates to a method for propagation of potatoes. More particularly, the present invention relates to a method for producing potatoes, for example, a potato tuber corm of a taro (Colocasia esculenta), a konjak (Amorphophallus konjac), a jack-in-the pulpit (Pinellia ternata), a Scopolia japonica rhizome, a Chinese yam tuberous root (Dioscorea japonica), having a size sufficient to cultivate seed potatoes by a single cultivation in the soil, by tissue culture in a short period of time.

BACKGROUND OF THE INVENTION

A variety of methods have been hitherto known to propagate potatoes by tissue culture.

There is known a method for obtaining potato tubers which comprises culturing a tissue of potato, removing roots and leaves from the obtained plant and subjecting the stem to liquid culture [CIP Circular, vol. 13, No. 4, December, pages 1 to 5 (1985); Plant Cell, Tissue and Organ Culture, 7:3 to 10 (1986)].

According to this method, the culture is performed by charging medium in a flask very thinly; thus, potato tubers are formed in the aerial phase and their numbers are not so large.

There is also known a method for propagation which comprises culturing a potato tuber and culturing the obtained plant, while repeatedly dividing it [American Potato Journal, 55: 691–701 (1978)]. However, even in the most efficient method, only 140 plants are obtained in 16 weeks. There is known a method for efficient propagation of small-sized potato tubers (Soshiki Baiyo (Tissue Culture), 11 (9), 391–395, 1985). The potato tubers formed by this method are of an adzuki size (about 0.1 g) to of an peanut size (about 0.7 g) in approximately 100 days after culture. In addition, single medium and culture conditions are utilized for the culture throughout the whole period. Further the culture is performed in a small-sized container and it is difficult to enlarge a culture scale.

It has been desired to develop a method of efficiently producing potato tubers having a weight of 1 g or more in mass culture.

In the case of Colocasia esculenta, Dioscorea japonica and Pinellia ternata, propagation of plants by tissue culture have succeeded, but a technique to efficiently propagate corm of a Colocasia esculenta, Pinellia ternata, and Dioscorea japonica tuberous root has not been developed [Yasai Shikenjo Hokoku A (Report A of the Vegetable Laboratories), 9: 1–46 (1981), Soshiki Baiyo (Tissue Culture), 11: 372–376 (1985)].

It has been desired to develop a method for efficient propagation of corm of Colocasia esculenta, Amorphophallus konjac, Pinellia ternata, a Scopolia japonica rhizome and a Dioscorea japonica tuberous root by tissue culture in large quantities.

DISCLOSURE OF THE INVENTION

According to the method of the present invention, plant materials obtained by culture of potato plants are transplanted into liquid medium, where the plant materials are cultured until they grow up to 15 to 30 cm in their average length. Then, in case that at least 90% of the obtained plants are not sunk in liquid medium, if necessary, fresh liquid medium is supplemented to allow at least 90% or more of plants to sink. While further continuing the cultivation, liquid mediuim is reduced with passage of time until 50 to 98% of the plants are exposed to the gas-phase, whereby tubers, rhizomes, corms or tuberous roots can be propagated in large quantities.

As the potatoes to which the present invention is applicable, mention may be made of a potato, Colocasia esculenta, Amorphophallus konjac, Pinellia ternata, Scopolia japonica, a Dioscorea japonica, etc.

Hereinafter the present invention will be described separately with a potato and other potatoes.

(I) In the case of a potato:

(A) Formation and propagation of plants by liquid culture

As plant materials used in the present invention, plant materials obtained by aseptically culturing a growing point, stem, leaf, root, cormus, etc. of potato plants in a conventional manner are used. The plant materials are transplanted into liquid medium in 5 to 50 pieces/l. As media to be usable, any of natural and synthetic media can be used so long as they suitably contain carbon sources, nitrogen sources, inorganic materials, etc.

As the carbon sources, sucrose, maltose, fructose, glucose, molasses, etc. can be used.

As the nitrogen sources, potassium nitrate, sodium nitrate, ammonium nitrate, calcium nitrate, ammonium sulfate, amino acids (glycine, glutamic acid, lysine, aspartic acid, etc.), yeast extract, meat extract, peptone, coconut milk, etc. can be used.

As the inorganic materials, potassium chloride, calcium chloride, manganese chloride, nickel chloride, cobalt chloride, aluminum chloride, iron chloride, magnesium sulfate, sodium sulfate, nickel sulfate, iron sulfate, manganese sulfate, zinc sulfate, copper sulfate, monopotassium phosphate, potassium iodide, boric acid, sodium molybdenate, etc. can be used.

If necessary, cytokinin, benzyl adenine (hereinafter referred to as BA), N-(2-chloro-4-pyridine)-N-phenylurea (hereinafter referred to as 4PU), kinetin, chlorocholine hydrochloride, abscisic acid, vitamin $B_1$, inositol, pyridoxine hydrochloride, nicotinic acid, thiamine hydrochloride, biotin, etc. may also be additionally added to the media.

As specific media, mention may be made of Murashige-Skoog medium, Erickson medium, White medium, Linsmayer-Skoog medium, etc.

The cultivation is performed in a glucose concentration of 60 g/l or less, preferably 25 to 35 g/l, in a medium depth of 12 cm or less, preferably 5 to 10 cm, at a temperature of 10° to 35° C. under an illuminance of 200 to 10,000 lux, pH of 4 to 8, an aeration amount of 0.01 to 0.5 vvm, preferably 0.05 to 0.2 vvm until an average length of the plant materials becomes 15 to 30 cm. In general, it takes 20 to 60 days.

(B) Induction and thickening growth of tuber

At least 90% or more of the plants, formed at Step (A) are sank into the medium used in Step (A) in which the glucose concentration is changed to 60 to 150 g/l, preferably 80 to 100 g/l. Then, while decreasing liquid medium with passage of time, cultivation is carried out at a temperature of 10° to 35° C., an illuminance of 200 lux or less, preferably in the dark and a pH of 4 to 8 until 50 to 98% of the plants are exposed to the aerial phase. In general, it takes 20 to 90 days.

To decrease liquid medium with passage of time, there are various methods, for example, a method in which liquid medium is evaporated off by aeration, a method in which liquid medium is discharged directly, etc. These methods may be used alone or in combination.

In the method in which liquid medium is evaporated off by aeration, an amount of aeration is in a range of 0.8 to 2.2 vvm which is higher in that of Step (A). In case that liquid medium is directly discharged, the liquid medium is appropriately discharged but, for example, when formation of potato tubers is observed around the interface between the medium and the aerial phase, an appropriate amount (for example, 10 to 20% of the total medium amount) is discharged and such discharging operation is performed 3 to 10 times. As such, a number of potato tubers can be obtained, among which many potato tubers grown to 1 g or more observed.

(II) In the case of other potatoes (taro, konjak, jack-in-the-culprit, Scopolia japonica and Chinese yam)

(A) Production and propagation of plants by liquid culture

Plants having an average length of 15 to +cm can be obtained using the same medium and cultivation method as in Step A of the case (I) of potato described above except for point, stem, leaf, root, cormus, or the like of a Colocasia esculenta, Amorphophallus konjac, Pinellia ternata, Scopolia japonica and Dioscorea japonica in a conventional manner.

(B) Induction and thickening growth of corm of Colocasia esculenta, Amorphophallus konjac, Pinellia ternata, Scopolia japonica rhizome and Dioscorea japonica tuberous root The plants formed in Step (A) are transplanted to the liquid medium as used in (I), step (A), a glucose concentration of which is charged to 60 to 150 g/l, preferably 80 to 100 g/l. Then, while allowing liquid medium to decrease with passage of time, cultivation is carried out at a temperature of 10° to 35° C., an illuminance of 200 lux or less, preferably in the dark and a pH of 4 to 8 until 50 to 98% of the plants are exposed to the aerial phase. In general, it takes 20 to 90 days.

To decrease liquid medium with passage of time, there is, for example, a method in which liquid medium is evaporated off by aeration (0.8–2.2 vvm).

BEST MODE TO PRACTICE OF THE INVENTION

EXAMPLE 1

Potato cormus were transplanted to 10 ml of Murashige-Skoog medium having a composition of Table 1, charged in a test tube having a diameter of 25 mm and a length of 125 mm and cultivated at 25° C. and 2500 lux for about a month under continuous lighting to obtain 20 plants of the potato grown to about 10 cm. Then, the plants were divided by every joint and then transplanted to a jar fermenter of a 16 l volume containing 5 l of liquid medium (depth of medium: 9 cm) obtained by removing agar from the medium shown in Table 1. Cultivation was performed at 25° C. in an aeration amount of 0.1 to vvm for 3 weeks under continuous lighting at 4000 lux to give plants grown to an average length of 20 cm. Then, after the medium was wholly removed, 10 l of liquid medium in which agar was removed from the medium shown in Table 1 and sucrose was changed to 9% (w/v) was again charged in a 16 l jar fermenter (depth of medium: 18 cm) followed by cultivation in the dark at 25° C. in an aeration amount of about 0.1 vvm. After adding the medium, formation of tubers was obviously noted mainly around the interface between the medium and the aerial phase in 5 days. Therefore, after discharging 2 l of the medium 5 days after the addition of medium to reduce the liquid surface of the medium, cultivation was performed, whereby formation of tubers was further observed around the interface of the medium and the aerial phase. Discharge of the medium (about 2 l) was repeated 4 times every 5 days to form tubers. The formed tubers continued to grow since then. The cultivation was completed in 45 days after the addition of medium. The amount of the medium remained was 0.8 l (depth of medium: 1 cm). About 95% of the plants was exposed to the aerial phase but not blighted. About 370 tubers in total were obtained around the interface of the medium and the aerial phase as well as at the aerial phase. Among them, about 80 tubers weighing 1 g or more were counted.

TABLE 1

| Murashige-Skoog Medium | |
|---|---|
| Ammonium nitrate | 1650 mg |
| Potassium nitrate | 1900 mg |
| Calcium chloride dihydrate | 440 mg |
| Magnesium sulfate heptahydrate | 370 mg |
| Potassium dihydrogenphosphate | 170 mg |
| $Na_2$.EDTA dihydrate | 37.3 mg |
| Ferric sulfate heptahydrate | 27.8 mg |
| Boric acid | 6.2 mg |
| Manganese sulfate tetrahydrate | 22.3 mg |
| Zinc sulfate heptahydrate | 8.6 mg |
| Potassium iodide | 0.83 mg |
| Sodium molybdenate dihydrate | 0.25 mg |
| Cuprous sulfate | 0.025 mg |
| Cobalt chloride | 0.025 mg |
| Vitamin $B_1$ | 0.40 mg |
| Inositol | 100 mg |
| Pyridoxine hydrochloride | 0.50 mg |
| Nicotinic acid | 0.50 mg |
| Glycine | 2.00 mg |
| Sucrose | 30.0 g |
| Agar | 8.0 g |

The components described above was dissolved in deionized water to make up 1 l. A pH of the solution was adjusted to 6.2 with 0.1N sodium hydroxide aqueous solution and separately charged in incubators followed by sterilization at 121° C. for 20 minutes.

EXAMPLE 2

Potato cormus were transplanted to 10 ml of Murashige-Skoog medium having a composition of Table 1, charged in a test tube having a diameter of 25 mm and a length of 125 mm and cultivated at 25° C. and 2500 lux under continuous lighting to obtain plants of the potato grown to about about 10 cm. Then, the plants were cut by every joint and 100 pieces obtained were then transplanted to a 8l-jar fermenter containing 2 l of liquid medium (depth of medium: 8 cm) obtained by removing agar from the medium shown in Table 1. Cultivation was performed at 25° C. in an aeration amount of 0.1 vvm for 4 weeks under continuous lighting at 4000 lux to give plants grown to an average length of 25 cm.

Then, after the medium was wholly removed, 6 l of liquid medium in which agar was omitted from the medium shown in Table 1 and sucrose was changed to 9% (w/v) was again charged in a 8 l-jar fermenter (depth of medium: 23 cm) followed by cultivation in the dark at 25° C. in an aeration amount of 0.8 vvm for 4 weeks. The amount of the medium remained was approximately 2 l (depth of medium: 8 cm). About 70% of the plants was exposed to the aerial phase but not blighted. About 390 potato tubers (weight: about 300 g) were obtained. Among them, about 110 tubers weighed 1 g or more. On the other hand, cultivation was performed in a similar manner except that the aeration amount in the cultivation described above was changed to 0.1 vvm. The amount of the medium remained was approximately 5.2 l (depth of medium: 19 cm). About 250 potato tubers (weight; about 210 g) were obtained. Among them, about 80 tubers weighing 1 g or more were counted.

EXAMPLE 3

While observing corm buds of Colocasia esculenta (species: Ishikawa Wase) with a stereoscopic microscope, their growth points were aseptically collected. The growth points were transplanted to 10 ml of Murashige-Skoog medium having a composition of Table 1, charged in a test tube having a diameter of 25 mm and a length of 125 mm and cultivated at 25° C. and 2500 lux for about 3 months under continuous lighting. The obtained plants were transplanted to a 300 ml-flask containing 100 ml of liquid medium obtained by removing agar from the medium shown in Table 1. Rotary spinner culture (180 r.p.m.) was performed at 25° C. under continuous lighting at 2500 lux. Two months after the culture, 250 plants were obtained. After aseptically taking out of the flask, the plants were aseptically divided into 10, which were transplanted to a 300 ml-flask containing 100 ml of liquid medium having the same composition as described above. Rotary spinner culture (180 r.p.m.) was performed at 25° C. under continuous lighting at 2500 lux for a month to propagate the plants. Similar rotary spinner culture (180 r.p.m.) was performed every other month to propagate the plants. Similar operations were repeated 20 times every other month to propagate the plants. As the result, the number of the plants gradually increased every subculture to obtain masses of 700 plants in average densely grown per flask. The thus subcultured and propagated plants (3 flasks) were transplanted to a 8 l-jar fermenter containing 6 l of liquid medium (depth of medium: 23 cm) obtained by removing agar from the medium shown in Table 1 and the concentration of sucrose was changed to 9% (w/v). Cultivation was performed at 25° C. in an aeration amount of 0.1 vvm for a month under continuous lighting at 2500 lux to give plants grown (an average length of 23 cm). Then, when cultivation was performed for additional one month in an aeration amount increased to 2 vvm but without changing the other conditions, the liquid medium was rapidly evaporated off by aeration so that the propagated plants were successively exposed from the liqiud medium into the aerial phase. One month after, the amount of the medium became 1.2 l exposed into the aerial phase but not blighted. At this point of time, the cultivation was completed and the plants were taken out. The basal parts of almost all plants were thickened and became corms. 2900 taro corms were obtained per jar fermenter. The weight was 0.8 kg in total and the corm weighed 0.3 g in average. In this case, the number of corm weighing more than 1 g was 370. In contrast, cultivation was performed for 2 months in an aeration amount of 0.1 vvm without changing the aeration amount during the course of cultivation; in this case, the medium was 4.7 l (depth of medium: 18 cm) at the time when the cultivation was completed. 430 Colocasia esculenta corms were obtained per jar fermenter. The weight was 130 g in total and a weight of corm was approximately 0.3 g in average. Further merely 65 corms weighing 1 g or more were counted.

EXAMPLE 4

Amorphophallus konjac corms were wrapped with water-adsorbing paper impregnated with 500 ppm of BA and further wrapped with vinyl so as to prevent moisture from evaporation. After allowing to stand at 25° C. for 7 days, about 100 auxiliary buds per corm were grown by 3 to 10 mm. While observing these buds with a stereoscopic microscope, the growth point parts were aseptically collected in a size of 0.2 mm or less. The growth point parts were transplanted to 10 ml of Murashige-Skoog medium having a composition of Table 1 and supplemented with 4 PU in a concentration of 1 mg/l, charged in a test tube having a diameter of 25 mm and a length of 125 mm and cultivated at 25° C. and 2500 lux for about 5 months under continuous lighting to obtain plants. The obtained plants were aseptically divided into 10 and further subcultured in the same medium as described above to propagate them. After repeating subculture propagation 5 times as such, the obtained plants (corresponding to 20 test tubes) were transplanted to a 8 l-jar fermenter containing 6 l of liquid medium (depth of medium: 23 cm) obtained by removing agar from the medium shown in Table 1 and changing the concentration of sucrose to 9% (w/v). Cultivation was performed at 25° C. in an aeration amount of 0.2 vvm for 60 days under continuous lighting at 2500 lux to give plants grown (an average length of 18 cm). Then, when cultivation was performed for an additional one month in an aeration amount increased to 1.5 vvm but without changing the other conditions, the liquid medium was rapidly evaporated off by aeration so that the propagated plants were successively exposed from the liquid medium into the serial phase. One month after, the amount of the medium became 1.7 l (depth of medium: 6 cm) and about 60% of the plants were exposed into the aerial phase but not blighted. At this point of time, the cultivation was completed to obtain 1800 Amorphophallus konjac corms per jar fermenter. The weight was 1.2 kg in total and weight of a corm was 0.7 g in average. Further, the number of corms weighing 1 g or more was 270.

In contrast, cultivation was performed for 2 months in an aeration amount of 0.2 vvm without changing the aeration amount during the course of cultivation; in this case, merely 47 Amorphophallus konjac corms were obtained.

EXAMPLE 5

While observing buds of Pinellia ternata corms with a stereoscopic microscope, the growth points were aseptically collected. The growth points were transplanted to 10 ml of Murashige-Skoog medium having a composition of Table 1, charged in a test tube having a diameter of 25 mm and a length of 125 mm and cultivated at 25° C. and 2500 lux for about 3 months under continuous lighting to obtain plants. Hereafter the obtained plants were cultivated in a manner similar to Example 3. The obtained plants (corresponding to 3 flasks) were transplanted to a 8 l-jar fermenter containing 6 l of liquid medium (depth of medium: 23 cm) obtained by removing agar from the medium shown in Table 1 and changing the concentration of sucrose to 9% (w/v). Cultivation was performed at 25° C. in an aeration amount of 0.1 vvm for 40 days under continuous lighting at 2500 lux to give plants grown (an average length of 20 cm). Then, when cultivation was performed for an additional one month in an aeration amount increased to 1.5 vvm, without changing the other conditions, the liquid medium was rapidly evaporated off by aeration so that the propagated plants were successively exposed from the liquid medium into the aerial phase. One month after, the amount of the medium became 2.0 l (depth of medium: 8 cm) and about 80% of the whole plants were exposed into the aerial phase and not blighted. At this point of time, the cultivation was completed to obtain 3600 Pinellia ternata corms per jar fermenter. The weight was 1.8 kg in total and corm weighed 0.5 g in average. Further, the number of corms weighing 1 g or more was 280. On the other hand, cultivation was performed for 2 months in an aeration amount of 0.1 vvm without changing the aeration amount during the course of cultivation; in this case, many plants were formed, but few corms were formed. 430 Pinellia ternata corms were obtained per jar fermenter. The weight was 130 g in total and corm weighed 0.3 g in average. Corms weighing 1 g or more were hardly obtained.

EXAMPLE 6

While observing buds of Dioscorea japonica stalks with a stereoscopic microscope, the growing points were aseptically collected. The growth points were transplanted to 10 ml of Murashige-Skoog medium having a composition of Table 1 and supplemented with 0.1 mg/l of naphthalene acetic acid and 0.1 mg/l of BA, charged in a test tube having a diameter of 25 mm and a length of 125 mm and cultivated at 25° C. and 2500 lux for about 5 months under continuous lighting to obtain the plants. The plants were transplanted to a 300 ml-flask containing 100 ml of liquid medium obtained by removing agar from the same medium as described above. Rotary spinner culture (180 r.p.m.) was performed at 25° C. under continuous lighting at 2500 lux. Two months after the culture 120 plants were obtained. After aseptically taking out of the flask, the plants were aseptically divided into 10, which were transplanted to a 300 ml-flask containing 100 ml of liquid medium having the same composition as described above. Rotary spinner culture (180 r.p.m.) was performed at 25° C. under continuous lighting at 2500 lux for two months to propagate the plants. Similar operations were repeated 3 times every two other months to propagate the plants. The thus propagated plants (corresponding to 3 flasks) by subculture were transplanted to a 8 l-jar fermenter containing 6 l of liquid medium (depth of medium: 23 cm) obtained by changing the concentration of sucrose in the medium shown in Table 1 to 9% (w/v). Cultivation was performed at 25° C. in an aeration amount of 0.1 vvm for 2 months under continuous lighting at 2500 lux to give plants grown (an average length of about 24 cm). Then, when cultivation was performed for further two months in an aeration amount increased to 2 vvm without changing the other conditions, the liquid medium was rapidly evaporated off by aeration so that the propagaged plants were successively exposed from the liquid medium into the aerial phase. One month after, the amount of the medium became 0.7 l (depth of medium: 3 cm) and about 85% of the whole plants were exposed into the aerial phase and not blighted. At this point of time, the cultivation was completed to obtain 1900 Dioscorea japonica tuberous roots per jar fermenter. The weight was 0.4 kg in total and a tuberous root weighed 0.2 g in average. On the other hand, cultivation was performed for 4 months in an aeration amount of 0.1 vvm without changing the aeration amount during the course of cultivation; in this case, the amount of liquid medium was 4.7 l (depth of medium: 18 cm) at the time when the cultivation was completed and 800 tuberous roots were obtained per jar fermenter. The weight was 140 g in total and a tuberous root weighed about 0.18 g in average.

EXAMPLE 7

While observing buds of Scopolia japonica rhizomes with a stereoscopic microscope, the growing points were aseptically collected in a size of about 3 mm. The collected buds were transplanted to 10 ml of Murashige-Skoog medium having a composition of Table 1, charged in a test tube having a diameter of 25 mm and a length of 125 mm and cultivated at 25° C. and 2500 lux for about 2 months under continuous lighting to obtain the plants. The plants were transplanted to 10 ml of Murashige-Skoog medium having a composition of Table 1 and supplemented with BA In a concentration of 1 mg/l, charged in a test tube having a diameter of 25 mm and a length of 125 mm and cultivated at 25° C. and 2500 lux for 40 days under continuous lighting to obtain the plants. The plants were aseptically divided into 10, which were transplanted to a medium having the same composition as described above, and subcultured in a similar manner to further propagate the plants. The thus propagated plants (20 pieces) were transplanted to a 8 l-jar fermenter containing 6 l of liquid medium (depth of medium: 23 cm) obtained by removing agar from the medium shown in Table 1, supplementing 1 mg/l BA and changing the concentration of sucrose to 9% (w/v). Cultivation was performed at 25° C. in an aeration amount of 0.1 vvm for 2 months under continuous lighting at 2500 lux to give plants grown (an average length of 20 cm). Then, when cultivation was performed for further 1.5 months in an aeration amount increased to 1 vvm, without changing the other conditions, the liquid medium was rapidly evaporated off by aeration so that the propagated plants were successively exposed from the liquid medium into the aerial phase. One end half months after, the amount of the medium became 2 l (depth of medium: 8 cm) and about 50% or more of the whole plants were exposed into the aerial phase and not blighted. At this point of time, the cultivation was completed and the plants were taken out; rhizomes were formed on the basal parts of the plants and 670 rhizomes were obtained per jar fermenter.

On the other hand, cultivation was performed for 3.5 months in an aeration amount of 0.1 vvm without changing the aeration amount during the course of cultivation; in this case, merely 420 rhizomes were obtained.

We claim:

1. A method for in vitro propagation of potato plants, of forcing such plants and of inducing propagules to form mini-tubers of enhanced size, the methods including the steps of:
   transplanting a potato plant initiate, the length of which does not exceed 10 cm, said plant initiate having at least a bud, said plant initiate obtained by culture of potato plant material in a first sparged liquid medium of about 3% sucrose content;
   culturing the plant initiate under an illuminance of 200 to 10,000 lux until an average length thereof reaches a length of 15 to 30 cm;

transferring the resulting plant to a second sparged liquid medium, said second sparged liquid medium containing about 9% sucrose;

maintaining a quantity of the second sparged liquid medium sufficient to cover at least 90% of the resulting plant for a preselected period of time; and, while further performing culture, inducing the formation of mini-tubers by reducing illuminance to not greater than 200 lux, and decreasing said second sparged liquid medium with passage of time until 50 to 98% of the plant is exposed to the atmosphere, until at least one mini-tuber is formed.

* * * * *

UNITED STATES PATENT AND TRADEMARK OFFICE
CERTIFICATE OF CORRECTION

PATENT NO. : 5,034,327
DATED : July 23, 1991
INVENTOR(S) : Takayama, et al

It is certified that error appears in the above-identified patent and that said Letters Patent is hereby corrected as shown below:

Title page, right column, line 3 amend "Want" to read --Wang--

Column 2, lines 51 and 62, amend "glucose" to read --sucrose--

Column 3, line 35, amend "glucose" to read

--sucrose--

Signed and Sealed this

Thirtieth Day of March, 1993

Attest:

STEPHEN G. KUNIN

Attesting Officer      Acting Commissioner of Patents and Trademarks